United States Patent [19]
Huille et al.

[11] Patent Number: 5,904,936
[45] Date of Patent: May 18, 1999

[54] PARTICLES BASED ON POLYAMINO ACID(S) AND CAPABLE OF BEING USED AS DELIVERY VEHICLES FOR ACTIVE PRINCIPLE(S) AND METHOD FOR PREPARING THEM

[75] Inventors: Sylvain Huille, Lyons; Alain Lemercier, St Bonnet de Mure; Gérard Soula, Meyzieu, all of France

[73] Assignee: Flamel Technologies, Venissieux Cedex, France

[21] Appl. No.: 08/621,438

[22] Filed: Mar. 25, 1996

[30] Foreign Application Priority Data

Mar. 28, 1995 [FR] France .................................. 95 03978

[51] Int. Cl.$^6$ ...................................................... A61K 9/14
[52] U.S. Cl. ......................... 424/489; 424/491; 424/401; 514/12; 514/21
[58] Field of Search ....................... 514/12, 21; 424/491, 424/489, 401

[56] References Cited

U.S. PATENT DOCUMENTS 4,351,337  9/1982  Sidman .................................. 424/491
4,976,968  12/1990 Steiner ................................... 128/217

OTHER PUBLICATIONS

Kreuter, *Pharm. Acta. Helv.*, 58, 7, 1983 CH, 196–209. (1983).

*Primary Examiner*—Johann Richter
*Assistant Examiner*—Patrick R. Delaney
*Attorney, Agent, or Firm*—Bacon & Thomas

[57] ABSTRACT

The present invention relates to delivery vehicles which are useful for the administration of active principles (APs), preferably medicinal or nutritional active principles, in particular via the oral or parenteral route.

The technical problem solved by the invention is that which consists in providing delivery vehicles composed of (nano)- or (micro)particles based on polyamino acids, and which are invert with respect to the AP (proteins), of controllable particle size, strong and inexpensive.

According to the invention, the particles have an average size of less than 200 μm and consist of a polyamino acid of the Leu/Glu type, in which Leu/Glu+Leu≧3% and the $M_w \geq 4{,}000$ D.

27 Claims, No Drawings

PARTICLES BASED ON POLYAMINO ACID(S) AND CAPABLE OF BEING USED AS DELIVERY VEHICLES FOR ACTIVE PRINCIPLE(S) AND METHOD FOR PREPARING THEM

The field of the present invention is that of delivery vehicles which are useful for the administration of active principles (APs) through cell membranes. These delivery vehicles permit the transport of APs under protection, inside a body, to their site of action. The AP is preferably a medicinal product or a nutrient for administration to an animal or human body via the oral, nasal, vaginal, ocular, subcutaneous, intravenous, intramuscular, intradermal, intraperitoneal, intracerebral, parenteral, and the like, routes, but it can also be a herbicide, a pesticide, an insecticide, a fungicide and the like, for the treatment of agricultural crops as an application for plant protection. For all these applications, the AP delivery vehicles are directed towards improving the bioavailability of the APs. These delivery vehicles can be, e.g., systems affording sustained release of AP.

The APs to which the invention relates more especially, but not restrictively, are, for example, proteins, glycoproteins, peptides, polysaccharides, lipopolysaccharides, oligonucleotides and polynucleotides. The present invention relates, more specifically, to particles—advantageously of the submicron- and/or micron-sized type—based on polyamino acids and intended for use as delivery vehicles for APs, especially medicinal APs. They are hence Delivery Particles (DPs), among which, on the one hand Nanodelivery Particles (NDPs), and on the other hand Microdelivery Particles (MDPs), will be distinguished hereafter in the present description, according to a nomenclature specific to the invention and which will be defined below.

The present invention relates both to the naked particles as such, and to the AP delivery vehicle systems consisting of the particles laden with the AP or APs in question.

The invention also relates to a method for preparing the said particles.

Progress in genetic engineering and the biotechnologies, together with the discoveries pertaining thereto of genetic tools, proteins and biologically active peptides, have permitted a blossoming of new medicinal active principles (APs) affording a high selectivity and intrinsic activity. These APs are, on the other hand, readily degraded in the body before reaching their site of therapeutic action, and their bioavailability is consequently very low. In the case of administration via the oral route, the gastrointestinal tract constitutes a formidable chemical and physical barrier for APs, which have, on the one hand to resist the degradation by the digestive system, and on the other hand to pass through the gastrointestinal epithelial membrane. In this connection, reference may be made, for example, to the review by M. J. HUMPHREY (Delivery System for peptide Drugs, edited by S. DAVIS and L. ILLUM, Plenum Press, N.Y., 1986), which mentions the low bioavailability of peptides administered orally.

Naturally, these hazards of transport and residence in the body are not limited to proteins, but also affect APs composed of genetic tools (oligonucleotides, polynucleotides, plasmids) capable of being employed in gene therapy techniques.

To remedy this, the proposal has been made to encapsulate APs in AP delivery particles, also known as DPs. The value of these encapsulation techniques is to protect and/or transport the AP to its site of therapeutic action by safeguarding it against damage by the body in order to increase its bioavailability.

Among all the materials which may be envisaged for the encapsulation of APs, polymers are being increasingly used on account of their intrinsic properties.

As regards the list of requirements which it is desired to obtain for such DPs, this is especially exacting and comprises, in particular, the following specifications:

1. It should be possible, advantageously, to be able to have at one's disposal DPs of average diameter between a fraction of a micron and a few microns, with a narrow particle size distribution, so as to be able to adapt the particle size of the DPs to the chosen mode of administration and/or the intended therapeutic site. For example, if a mucosal immunisation via the oral route is sought, the size of the DPs should be between 0.5 µm and 10 µm so that the DPs can enter the Peyer's patches and reach the lymphoid tissues. In the case of a subcutaneous administration, there is advantage in having at one's disposal DPs larger than 10 µm in size so that the particles do not re-enter the general circulation, where they are rapidly internalized by the reticuloendothelial system, but diffuse gradually from their injection site. This specification involves a dimensional control of the DPs, both on the particle size distribution of the DPs and on their average diameter, which represents a very intricate operation from a technological standpoint.

2. It is desirable that the DPs provide for protection of the AP up to the site of release. For example, in an oral administration of an AP composed of a vaccine, the latter would benefit from being protected throughout the length of the gastrointestinal tract.

3. It is preferable for the polymer constituting the DPs to be biocompatible and biodegradable and, better still, for it to be metabolized to products which are non-toxic to the body.

4. It is also advantageous for the polymer constituting the DPs not to induce an immune response (not to be immunogenic).

5. Lastly, it is also preferable for the DPs to be obtainable by a method which does not denature the AP. Thus, the use of organic solvents and/or high temperatures is to be ruled out.

A large number of previous technical proposals have attempted in vain to satisfy these collective specifications. Hence the approaches used hitherto fulfil the requirements only partially and incompletely.

Among these unsuccessful proposals, there may be mentioned one according to U.S. Pat. No. 5,286,495, which relates to a method for the encapsulation of proteins in an aqueous phase using materials consisting of alginate and polylysine. This method is presented as non-denaturing for proteinaceous APs on account of the fact that no use is made of an organic solvent, damaging chemical reagent or high temperature. However, the technique of manufacture of the DPs employed, by vaporization, does not enable particles smaller than 35 µm in size to be produced, which does not enable them to be internalized by the cells of the body.

Furthermore, emulsion techniques are commonly used to prepare microparticles a few microns in size.

For example, Patent Applications WO 91/06,286 and WO 91/06,287 describe methods for the formation of particles in emulsion in which:

either a hydrophobic protein chosen from collagen, casein, keratin and, preferably, prolamines, or a biocompatible and biodegradable polymer, such as poly(lactics) or poly(ortho esters), is used as polymer.

The AP can be hydrophobic or hydrophilic but, in the latter case, the double emulsion technique is recommended.

The size of the microparticles is approximately 100 μm, and preferably between 50 nm and 100 μm.

Patent Application WO 89/08,449 also makes reference to encapsulation by emulsion in order to incorporate APs in microparticles of poly(lactics) smaller than 10 μm in size. And it is specified in this document that this size is a maximum limit for absorption through the lymphoid tissues of the mucosae (oral, nasal, rectal and ophthalmological administrations).

The emulsion techniques are very attractive in principle, since they enable most APs to be employed in microparticles whose particle size can be controlled up to sizes of the order of 1 μm. However, in these techniques, use is made of organic solvents to solubilize the polymers constituting the particles. These solvents are, e.g., ketones, alcohols, amides or mixtures thereof. And it unfortunately proves to be the case that these solvents can be denaturing, in particular for peptide or polypeptide APs.

Biocompatible DPs, formed in aqueous solution without excessive temperature rise and called proteinoids, are also known. These DPs have been described since 1970 by W. FOX and K. DOSE in "Molecular Evolution and the origin of Life", published by Marcel DEKKER Inc. (1977).

On the basis of this work, Patent Application WO 88/01, 213 ('1213) proposes an AP delivery system based on proteinoids. The polymer used is a mixture of artificial polypeptides obtained by thermal condensation of synthetic or natural amino acids and/or of small peptide chains. The chosen mode of condensation leads to branched oligomers which are hence only very sparingly soluble. A selection is then performed by filtration of these branched oligomers so as to recover the water-soluble fractions. This fraction is necessarily composed of branched crosslinked products of very small mass. The microparticles according to this invention are obtained by changing the pH, which creates the precipitation of the branched oligomers as proteinoids.

When the solution in which the precipitation takes place contains APs in solution, a portion of them is entrained in the proteinoid during its formation.

The drawbacks of this system are:

a low degree of encapsulation, an intricate method of purification, a non-regular (non-alpha-peptide) linkage of the amino acids due to the mode of synthesis which does not enable it to be asserted that the enzymatic degradation reactions will be identical to those of an alpha-polyamino acid, lastly, the use of a large number of different amino acid monomers, which can induce an immune response.

Patent Application WO 93/25,589 covers improvement of the method for the synthesis of proteinoids by thermal condensation of amino acids.

The proteinoids are, in this instance also, formed from branched oligomers of low molecular masses, consisting of irregular linkages of amino acids. The water-soluble character of these branched oligomers is obtained:

on the one hand by the use of very low masses (between 250 and 2,400), corresponding to very short linkages of 2 to 20 amino acids, on the other hand by the choice of the starting amino acids.

As before, the proteinoids are formed by precipitation triggered by lowering the pH of the water-soluble branched oligomers. When this precipitation takes place in the presence of water-soluble APs, a portion of the latter is entrained in the proteinoid during its formation. The degrees of encapsulation remain modest: from 20 to 40%. Moreover, the lowering of the pH may be detrimental to some APs.

In addition, the fact of having to carry out the encapsulation at a particular pH constitutes a troublesome methodological constraint, and limits the use of these microparticles to the pH of precipitation of the proteinoids, which does not necessarily correspond to biological pH values. For example, the pH can vary from 2 to 7.5 in the gastrointestinal tract.

Mention will also be made, for the record, of U.S. Pat. No. 4,351,337, which belongs within a different field from that of the delivery of APs which is specific to the invention. This patent discloses fixed implants localized in quite definite places in the body. Hence such implants bear no relationship to forms which can be administered, e.g., orally or by injection. The said implants can be, inter alia, spherical microcapsules of the matrix or coated type, of the order of 400 to 800 μm in size (FIGS. 8–9) and hence much larger than the sizes of the order of 0.5 μm and 10 μm required for the microparticles to be internalized by the cells of the body. These implants are produced from polymer materials of the polyamino acid kind (Leu/Glu in particular). The shaping of these implants is performed, e.g., using solutions of polyamino acids in dioxane, which is evaporated off at the end.

In this state of knowledge, one of the essential objectives of the present invention is to provide DPs, especially submicron- and micron-sized DPs, based on polyamino acids and capable of being used as delivery vehicles for an active principle (AP), especially a medicinal and/or nutritional AP, for administration of the said AP to a human or animal body, these DPs fully satisfying the list of requirements detailed above and repeated below:

1. It should be possible, advantageously, to be able to have at one's disposal DPs of average diameter between a fraction of a micron and a few microns, with a narrow particle size distribution, so as to be able to adapt the particle size of the DPs to the chosen mode of administration and/or the intended therapeutic site. For example, if a mucosal immunisation via the oral route is sought, the size of the DPs should be between 0.5 μm and 10 μm so that the DPs can enter the Peyer's patches and reach the lymphoid tissues. In the case of a subcutaneous administration, there is advantage in having at one's disposal DPs larger than 10 μm in size so that the particles do not re-enter the general circulation, where they are rapidly internalized by the reticuloendothelial system, but diffuse gradually from their injection site. This specification involves a dimensional control of the DPs, both on the particle size distribution of the DPs and on their average diameter, which represents a very intricate operation from a technological standpoint.

2. It is desirable that the DPs provide for protection of the AP up to the site of release. For example, in an oral administration of an AP composed of a vaccine, the latter would benefit from being protected throughout the length of the gastrointestinal tract.

3. It is preferable for the polymer constituting the DPs to be biocompatible and biodegradable and, better still, for it to be metabolized to products which are non-toxic to the body.

4. It is also advantageous for the polymer constituting the DPs not to induce an immune response (not to be immunogenic).

5. Lastly, it is also preferable for the DPs to be obtainable by a method which does not denature the AP. Thus, the use of organic solvents and/or high temperatures is to be ruled out.

Another essential objective of the invention is to provide DPs based on polyamino acids which are of a controllable and adjustable average particle size, the latter being within orders of magnitude varying from 200 µm (MDP) down to a few nanometres (NDP).

Another essential objective of the invention is to provide DPs which are simple to prepare (non-damaging pH), stable at any pH between 4 and 13 and non-immunogenic.

Another essential objective of the invention is to provide DPs based on polyamino acids which are industrially feasible and economic and which are capable of being loaded with AP with high degrees of loading.

Another essential objective of the invention is to provide a method for preparing MDP's and/or NDP's based on polyamino acids and capable of being used as AP delivery vehicles, the said method having to be inexpensive, simple to carry out and non-denaturing for the APs, and having, in addition, to permit a fine control of the average particle size of the particles obtained (maximum 200 µm).

Another essential objective of the invention is the use of the abovementioned particles for the preparation of medicinal products (e.g. vaccines) and/or of nutrients, especially for oral, nasal, vaginal, ocular, subcutaneous, intravenous, intramuscular, intradermal, intraperitoneal, intracerebral or parenteral administration of active principles such as proteins, glycoproteins, peptides, polysaccharides, lipopolysaccharides, oligonucleotides and polynucleotides.

Another essential objective of the invention is to provide a medicinal product of the type comprising a system affording sustained release of AP, which is biocompatible and which gives rise to a high bioavailability of the AP.

Another essential objective of the invention is to provide a system for the delivery of vaccines which is non-immunogenic intrinsically and in combination with one or more antigens.

The objectives relating, inter alia, to the products are achieved by the present invention, which relates to particles for the delivery of active principle(s), of the type based on polyamino acid(s) and of average size smaller than 200 µm, characterized:

in that their constituent polyamino acids comprise at least two types of recurring amino acid, AAN and AAI:
the type AAN corresponding to a hydrophobic neutral amino acid,
and the type AAI corresponding to an amino acid having an ionizable side chain, at least a portion of the type AAI recurring amino acids being in ionized form,
the recurring amino acids of each type, AAN and AAI, being identical to or different from one another,
and in that the weight average molar mass $M_w$ of the polyamino acids is not less than 4,000 D, and preferably not less than 5,000 D.

The Applicant is to be credited with having carried out a selection from the polyamino acids so as to use only those having the feature of being non-water-soluble, forming stable colloidal suspensions over a wide pH range compatible with the pH values of physiological media for the intended applications, and containing a first type of AAN monomers which is composed of a hydrophobic neutral amino acid, and at least one second type of monomers which is composed of an AAI amino acid, characterized by a side chain having carboxyl functionality (Glu, Asp), ionizable at physiological pH values which are non-denaturing for proteins.

According to a characteristic of the invention, these polyamino acids (PAAs) are linear, and still more preferably they possess α-peptide linkages.

Advantageously, the PAAs selected as constituent elements of the DPs of the invention can be "block" PAAs and/or "statistical" PAAs. "Block" PAAs are those having a sequential and alternating ordered structure in which the amino acids are distributed in blocks along the polymer chains. "Statistical" PAAs are those having a sequential and random disordered structure in which the amino acids are distributed in a non-regular manner along the polymer chains.

As regards the AAN/AAI+AAN mole ratio, this is dependent on the "block" or "statistical" structure of the PAAs. Thus, this mole ratio is:

$\geq 6\%$, and preferably $\geq 15\%$ for the "block" PAAs,
$\geq 20\%$, and preferably $\geq 25\%$ for the "statistical" PAAs.

According to another characteristic of the invention, the mass of the selected polyamino acids is high.

In this connection, it should be pointed out that the preferred weight-average molar mass ($M_w$) for the polyamino acids employed in the context of the invention is defined differently according to the type of polyamino acid envisaged. Thus, $M_w \geq 5,500$ D, is preferably between 6,500 D and 200,000 D and still more preferably between 8,000 and 20,000 D for the "block" polyamino acids as defined above. While, for the "statistical" polyamino acids which are also defined above, $M_w \geq 10,000$ D is preferably between 20,000 D and 500,000 D and more preferably between 20,000 D and 150,000 D.

These polyamino acids form amphiphilic polymers capable of interacting with both hydrophobic substances and hydrophilic substances, endowing them with noteworthy properties as surfactants or as dispersants. However, in addition to their amphiphilic properties, these polyamino acids are distinguished by a novel and altogether unexpected property: the polyamino acid chains in aqueous solution associate spontaneously and form particles which can associate with proteins. In practice, these particles preferably form matrices within which the PA or PAs is/are dispersed. The preferred linear structure by α-peptide linkages and the high molar mass are also important characteristics of these polyamino acids.

These non-water-soluble PAAs are distinguished by a novel and altogether unexpected property. When placed in contact with an aqueous solution, they spontaneously form therein a colloidal suspension of nanoparticles (NDPs) capable of aggregating into microparticles (MDPs). In addition, proteins in solution can associate spontaneously with these particles to form particles loaded with APs.

This discovery is all the more surprising for the fact that the teaching of Application WO 93/25,583 was likely instead to encourage a person skilled in the art to direct his searches for an ideal material for the "encapsulation" of proteins towards products other than polyamino acids. In effect, the large number of trials carried out and given in Patent Application WO 93/25,583 suggest that, among all the polyamino acids tested, only those selected and claimed are suitable. Only after an inventive step was the Applicant able to demonstrate that this was not the case by proposing another selection of polyamino acids having a behaviour different from those according to WO 93/25,583, these PAAs being, in particular:

linear PAAs of high molar masses (above 4,000 D), rather than small branched oligomers,
insoluble rather than soluble PAAs, and it is surprising that these insoluble PAAs spontaneously form a colloidal suspension of NDPs and that proteins associate spontaneously with these NDPs.

The preferred polyamino acids are synthetic linear polymers advantageously composed of α-amino acids linked via peptide bonds. There are a large number of synthetic techniques for forming block or statistical polymers, polymers containing multiple chains and polymers containing a specified amino acid sequence (see Encyclopedia of polymer Science and Engineering, volume 12, page 786; John Wiley & Sons). A large number of amino acid and peptide derivatives have been used as monomers for the preparation of polyamino acids. However, the monomers most commonly used are N-carboxy-α-amino acid anhydrides whose preparation is given, for example, in Biopolymers, 15, 1869 (1976). The techniques of polymerization of these monomers are known to a person skilled in the art, and are detailed in the work by H. R. KRICHFELDORF "α-Aminoacid-N-Carboxy Anhydrides and Related Heterocycles" Springer Verlag (1987).

The synthesis techniques generally involve protecting the reactive functions of amino acids having ionizable side chains so that they do not interfere during the polymerization step. It follows from this that a step of deprotection is necessary in order to re-establish the functionality of the ionizable side chains of the polymer. There may be mentioned, for example, methods of deprotection by saponification of the methyl esters [STAHMAN et al., J. Biol. Chem., 197, 771 (1952); KYOWA HAKKO, FR 2,152,582) or of debenzylation [BLOUT et al., J. Amer. Chem. Soc., 80, 4631 (1858)].

Advantageously, the DPs have an average polyamino acid concentration varying from 0.01% to 25% dry weight, and preferably from 0.05 to 10% dry weight.

According to a preferred embodiment of the particles according to the invention, the AAN or AANs is/are chosen from the following list, namely Leu—Ile—Val—Ala—Pro—Phe—and mixtures thereof, and the AAI or AAIs is/are composed of Glu and/or Asp.

Still more preferably, the particles of the invention are characterized in that their constituent polyamino acids contain a single type of AAI monomers preferably corresponding to Glu, and a single type of monomers preferably corresponding to Leu.

The fact of limiting the number of comonomers to only two, namely one of type AAN and one of type AAI, enables the immunogenicity of the particles to be minimized. This is a significant advantage of this preferred embodiment of the invention.

The size of the particles of polyamino acids selected forms part of the fundamental elements of the present invention. Advantageously, these particles have an average size of between 0.01 and 200 μm, with a narrow particle size distribution.

One of the great assets of the invention is the fact of having succeeded very well in controlling the average particle size of the particles and their particle size distribution. This control comes from the achievement of extremely small particle sizes, of the order of a few nanometres and of very low polydispersity, knowing that it is possible to increase the size of these nanoparticles by aggregation. While no limitation is imposed thereby, it is thus possible to distinguish two populations of particles as a function of their sizes.

The first of these populations groups together the particles of the NDP nanoparticle type, of average size between 0.01 μm and 0.5 μm, and preferably between 0.03 and 0.4 μm.

The second population comprises the particles of the MDP type, of average size larger than 0.5 μm, and preferably not exceeding 20 μm.

For the purposes of the invention, average particle size is understood to mean the arithmetic mean of the diameters by volume (D4.3) established by laser diffraction in the case of MDPs, and the diameter of gyration measured by elastic scattering of light in the case of NDPs.

The microparticles MDPs are advantageously obtained from the nanoparticles NDPs, e.g. by aggregation.

According to a variant, the microparticles comprise at least one aggregating agent.

According to a preferred characteristic of the invention, the particles comprise at least one active principle.

The control of the size of the MDPs and NDPs is achieved, in addition, by means of the composition of the polyamino acids, but also, for the same composition, by means of the ordered structure (alternating sequential, i.e. block: $S_1$) or disordered structure (random sequential, i.e. statistical: $S_2$).

The nomenclature which will be used in the present description for naming the polyamino acids is as follows: polyAAN1/AAN2/ . . . /AAI1/AAI2/ . . . A/B/C/D . . . , A, B, C, D . . . being the molar percentages of the amino acids. Furthermore, the ordered block structure is distinguished from the disordered or statistical structure by adding the term "block". For example, the statistical copolymer composed of 30% of leucine and 70% of glutamic acid is polyLeu/Glu-30/70, and the copolymer with the same composition and of block structure $(Leu)_n\text{-}(Glu)_m$ is polyLeu/Glu block-30/70.

According to a preferred embodiment of the invention, the particles are characterized in that AAI=Glu and AAN=Leu.

Besides the particles described above as a new product per se, the subject of the present invention is also a method for preparing particles based on polyamino acid(s) and capable of being used as delivery vehicles for active principle(s), characterized:

in that polyamino acids (PAAs) are employed:
comprising at least two types of recurring amino acids, AAN and AAI:
the type AAN corresponding to a hydrophobic neutral amino acid,
and the type AAI corresponding to an amino acid having an ionizable side chain,
the recurring amino acids of each type, AAN and AAI, being identical to or different from one another,
the AAN/AAI+AAN mole ratio being ≧3%, and preferably ≧5 %,
the weight average molar mass $M_w$ of the polyamino acid or acids being not less than 4,000 D, and preferably not less than 5,000 D,
in that a dispersion of these polyamino acids is produced in a liquid, preferably in a saline aqueous solution, whose pH has been adjusted to a value chosen in such a way that at least a portion of the type AAI amino acids is in ionized form,
and in that a colloidal solution of particles is thus collected.

The description of the characteristics of the PAAs given above in the context of the presentation of the particles may be transposed in its entirety into the present description relating to the method. This method is one of the ones enabling the NDP particles presented above to be obtained. Hence these particles can be those in which the AAN or AANs is/are chosen from the following list, namely Leu—Ile—Val—Ala—Pro—Phe—and mixtures thereof, and those in which the AAI or AAIs is/are composed of Glu and/or Asp.

Formation of the NDPs hence takes place in a simple manner, in a saline aqueous solution (for example) and at a pH chosen in such a way that at least a portion of the AAI monomers (identical to or different from one another in nature) is in ionized form. This spontaneous generation of nanoparticles, by dispersion of copolyamino acids in a saline medium, is noteworthy in its simplicity, economy and hence industrial feasibility.

Furthermore, it is possible by this method to avoid the organic solvents generally used to prepare this type of particle, and which are known to bring about the denaturation of proteins.

The conditions for obtaining these NDPs can be readily mastered by a person skilled in the art.

The formation of NDPs depends, on the one hand on the nature of the aqueous dispersion solution, and on the other hand on the characteristics of the polyamino acid.

The aqueous solutions for dispersion of the polyamino acids must satisfy certain conditions of pH and ionic strength. It will be readily understood, in effect, that the stability of the nanoparticles of polymers containing ionized groups depends on the ionic strength. As regards pH, this is of course dependent on the nature of the ionizable groups, of which it fixes the ionization fraction f. Thus, for carboxyl groups, f increases with the pH.

In any case, one of the definite advantages of the method according to the invention is to permit the spontaneous formation of NDPs independently of the pH over a wide pH range between 3 and 13, thereby amply covering the range of biological pH values and thus opening up a broad field of applications.

The NDPs of polyamino acids form colloidal solutions.

For these polyamino acids, the distinguishing characteristics of the NDP formation are:

i) the molar mass, 2i) the nature of the amino acids, 3i) the proportions of amino acids, 4i) the presence of linear, preferably α-peptide, linkages, 5i) the distribution of the amino acids along the polymer chains, in regular or random fashion, according to the "block" or "statistical" structures, respectively.

These characteristics are discussed below.

As regards the influence of the molar mass, it may be noted that the formation of NDPs results from the association of the amino acids between the polyamino acid chains, and that this association functions differently according to the structure and the molar mass of the polymer.

For polyamino acids of "statistical" structure, polymers of molar masses not less than 10,000 D, preferably between 20,000 D and 500,000 D and more preferably between 20,000 D and 150,000 D disperse readily in aqueous solution and form stable colloidal suspensions of NDPs. Under the same conditions, polymers of lower molar mass do not form stable colloidal suspensions; a portion of the particles precipitate, and the NDPs, maintained in dispersion, show little tendency to diffuse. Hence, the higher the molar mass of the polyamino acids, the more favourable the association of the polymer chains into NDPs.

In the case of polyamino acids of "block" structure, interchain association between blocks of identical amino acids is favoured, thereby permitting the use of polymer of lower molar mass than the polyamino acids of "statistical" structure. Polymers of molar masses not less than 5,000 D, preferably between 6,500 D and 200,000 D and more preferably between 8,000 D and 20,000 D disperse readily in aqueous solution and form stable colloidal suspensions of NDPs.

As regards the influence of the nature of the amino acids and the proportion thereof, it may be pointed out that, in the case of the PAAs of leucine and of glutamic acid, the fraction of leucine must be sufficiently high to prevent the polymer from being completely soluble and to provide for sufficient hydrophobic interactions for the polymer chains to associate into NDPs. These interchain interactions are favoured with the "block" polyamino acids, and the minimum fraction of leucine needed to form NDPs is smaller with the "block" polymers than with the "statistical" polymers. It has been possible to show, for example, that the critical concentration below which the polymer is soluble is between 20 and 30% for the "statistical" polymers of leucine and glutamic acid.

To carry out the preparation of NDPs according to the invention, the molarity of the saline solution is advantageously set at between $10^{-4}$ and 1 M, and preferably $10^{-2}$ M to 0.5 M approximately.

According to another practical detail of the invention, the polymer concentrations in the solution, expressed in % weight/volume, are chosen to be not less than $10^{-2}$, preferably between 0.05 and 30 and still more preferably between 0.05 and 5.

Inasmuch as one of the most noteworthy applications of the particles and the method for obtaining them according to the invention is the transport of active principles under protection in the human or animal body, it is advantageous, for this purpose, to arrange for at least one active principle to be dissolved in the liquid medium of formation of the particles.

This dissolution of the active principle, especially in the case of a proteinaceous and polypeptide active principle, preferably takes place before the introduction of the polyamino acids into the medium, so that a colloidal solution of particles loaded with active principle is obtained after this introduction.

While there is no wish to be bound by the theory, it may be supposed that the interaction between the AP and the polyamino acids is the outcome of hydrophobic and electrostatic associations.

In summary, the encapsulation according to the invention hence consists in:

bringing the AP to be encapsulated into aqueous solution, and in dispersing the polyamino acid in an aqueous solution, and then in mixing the colloidal suspension of nanoparticles thus formed with the solution of AP, or alternatively and preferably in dispersing polyamino acid directly in the solution of AP, so as to obtain spontaneously nanoparticles loaded with AP.

One of the major essential characteristics of the invention is that the phenomenon of association of the AP or APs with the particles is independent of the pH.

It has been seen above that the dispersion of the copolyamino acid in the liquid, preferably saline, medium constitutes a key step in the method for the preparation of particles, where appropriate loaded with AP, according to the invention. The method according to the invention is also distinguished by the fact that it comprises at least one additional step of aggregation of the nanoparticles (NDPs) into microparticles (MDPs), preferably with the aid of a salt and/or an acid and/or a polymer (advantageously a polyelectrolyte).

As a result of this characteristic of the method of the invention, it is possible to aggregate NDPs between 0.01 and 0.05 $\mu$m in size into MDPs between 0.05 and 200 $\mu$m, preferably between 0.05 and 20 $\mu$m and still more ideally between 0.05 and 10 $\mu$m in size.

This aggregation must be carried out under conditions which are non-denaturing for the AP, and the Applicant has found that the addition of salts or acids or cationic polymers in particular brings about aggregation of the NDPs into MDPs.

The addition of salts enables the ionic strength of the medium to be increased and causes aggregation of the NDPs by screening out the electrostatic repulsions between the particles. Furthermore, the salt may also act as an agent for crosslinking the carboxyl functions of the polyamino acids which are present at the surface of the particles, and thus cause their aggregation by complexing several carboxylic acids with the cation of the salt. In this case, it will be preferable to choose polycationic salts from those which form complexes with carboxylic acids, such as $Fe^{2+}$, $Fe^{3+}$, $Zn^{2+}$, $Ca^{2+}$, $Al^{2+}$, $Al^{3+}$ and $Cu^{2+}$ salts.

The addition of acids decreases the ionization fraction f by neutralizing the carboxyl functions of the polyamino acids, and thus brings about aggregation of the NDPs into MDPs. The ionization fraction at which aggregation takes place depends on the composition of the polyamino acid AAN/(AAN+AAI). The higher the proportion of AAI, the smaller this fraction. The acid which is added is advantageously a strong acid having a pKa lower than that of the carboxyl functions in the polyamino acids.

Cationic polymers act as aggregating agents by associating the NDPs; they form complexes between the carboxyl functions at the surface of the particles, which are thus linked to one another via the cationic polymer molecules.

The conditions of aggregation of NDPs into MDPs are set forth in the examples.

On completion of the method, with or without encapsulation of AP, the (nano)- and (micro)particles are recovered by any suitable means known per se. In practice, use may be made, for example, of centrifugation and lyophilization.

The active principle capable of being included or incorporated (preferably according to a matrix type arrangement) in the particles according to the invention, whether or not these particles are obtained by the method described above, is medicinal and/or nutritional. It is preferably chosen from:

proteins and/or peptides, among which those most preferably selected are: haemoglobins, cytochromes, albumins, interferons, antigens, antibodies, calatonin, erythropoietin, insulin, growth hormones, factor IX, interleukin or mixtures thereof, polysaccharides, heparin being selected more especially, nucleic acids, and preferably oligonucleotides of RNA and/or DNA, and mixtures thereof.

The APs which may be classified within the category of medicinal products and which are suitable for delivery by the particles according to the invention are vaccines.

As an example of a nutritional product, vitamins, amino acids and trace elements may be mentioned.

According to another of its aspects, the invention also relates to the use of these NDPs and MDPs loaded with AP, for the manufacture of medicinal products of the type comprising systems affording controlled release of AP.

Lastly, the present invention relates to medicinal products or pharmaceutical or nutritional specialities comprising the DPs loaded with AP and defined above.

In the case of medicinal products, these can be, for example, those which are preferably administrable via the oral, nasal, vaginal, ocular, subcutaneous, intravenous, intramuscular, intradermal, intraperitoneal, intracerebral or parenteral route.

The applications of the invention are not limited to the delivery or transport of AP of a medicinal or nutritional nature. In effect, it is entirely conceivable that the AP capable of being included or incorporated in the DP is at least one cosmetic or plant-protection product. Cosmetic applications which can be envisaged are, for example, compositions applicable transdermally. The plant-protection products in question can be, for example, herbicides, pesticides, insecticides, fungicides, and the like. The subject of the present invention is also plant-protection and cosmetic compositions comprising DPs loaded with AP of the type referred to above.

The examples which follow will enable better understanding of the invention to be gained, in its different product/method/application aspects. These examples illustrate the preparation of particles of polyamino acids loaded or otherwise with active principles, and they also present the structural characteristics and the properties of these particles.

EXAMPLES

I—Preparation of the Polyamino Acids Tested

The polymers employed in the examples are linear synthetic copolymers having block or statistical structures, based on leucine and glutamic acid. The polyamino acids have weight average molar masses $M_w$, determined by elastic scattering of light in the solvent trifluoroacetic acid, of between 50,000 D and 150,000 D.

These polymers are obtained from the copolymer of leucine and methyl glutamate, the functionality of the ionizable side chains of the sodium glutamate of which is re-established using the known methods of deprotection of methyl esters described, for example, by STAHMAN et al., J. Biol. Chem., 197, 771 (1952) or in the KYOWA HAKKO Patent FR 2,152,582.

The copolymer of leucine and methyl glutamate is obtained from the N-carboxy-α-amino acid anhydrides (NCAs) of leucine and of methyl glutamate whose preparation is given, for example, in Biopolymers, 15, 1869 (1976). The techniques used for the polymerization of NCAs to polymers having block or statistical structures are known to a person skilled in the art, and are detailed in the work by H. R. KRICHELDORF "α-Aminoacid-N-Carboxy Anhydrides and Related Heterocycles", Springer Verlag (1987).

Example 1

Synthesis of a "Statistical" Polyamino Acid, Poly (Leu/Glu) 50/50

Step 1
Copolymerization of NCA-Leu and NCA-Glu(OMe): Poly (Leu-Co-Glu(OMe)) 50/50

15.0 g of methyl glutamate N-carboxy anhydride (NCA-Glu(OMe): 0.08 mol) and 12.5 g of leucine N-carboxy anhydride (NCA-Leu: 0.08 mol) are introduced under a stream of nitrogen into a 1-l reactor equipped with a glass stirrer, a nitrogen inlet and an outlet connected to a bubbling device. 381 ml of dioxane are added and the reaction medium is brought to 40° C.

After dissolution of the NCAs, 24 ml of water are introduced, followed by 0.22 ml of triethylamine (equivalent to 1 mol % relative to the NCAs). Monitoring of the polymerization is performed by IR, by observing the disappearance of the carbonyl bands at 1,860 and 1,790 $cm^{-1}$. The polymerization time varies between 1.5 h and 3 h according to the composition of the monomers. After the bands have disappeared completely, the reaction medium is diluted with 380 ml of dioxane and then homogenized for 3 h at room temperature. The copolymer is recovered by precipitation in 5 l of water with efficient stirring. The product is filtered off and dried at 50° C. under vacuum for 12 h.

The mass of copolymer obtained is 18.4 g, equivalent to a 90% weight yield. $^1$H NMR (trifluoroacetic acid-d): 0.85 ppm (CH$_3$-Leu, 6H*0.5); 1.58 (CH$_2$ and CHMe$_2$Leu, 3H*0.5); 2.10 and 2.22 (CH$_2$-Glu, 2H*0.5); 2.58 (CH$_2$-Glu; 2H*0.5); 3.75 (CH$_3$-Glu, 3H*0.5); 4.62 (NCHCO-Leu, 1H*0.5); 4.70 NCHCO-Glu, 1H*0.5). Reduced viscosity (0.5 g/dl in trifluoroacetic acid) at 25° C.=2.2 dl/g.

Step 2

Hydrolysis of the Methyl Ester of Poly(Leu-Co-Glu(OMe)) 50/50

The copolymer obtained above (17.7 g) is placed in a reactor into which 354 ml of trifluoroacetic acid are added. The reaction medium is brought to 40° C. with stirring. When the copolymer has dissolved completely, 354 ml of water are added in small amounts. The reaction medium is kept stirring for 48 h.

The polymer is recovered by precipitation in 5 l of water. After filtration, it is suspended again and stirred in water for 0.5 h, then filtered and drained. Purification is performed by dialysis in water.

Yield 15.9 g (95%). $^1$H NMR (trifluoroacetic acid-d): identical to the starting polymers with one exception, the signal at 3.75 (CH$_3$-Glu) is greatly decreased or absent. In the present case, the content of residual esters is less than 1% relative to the glutamate monomers. Reduced viscosity (0.5 g/dl in trifluoroacetic acid) at 25° C.=0.95 dl/g.

Example 2

Synthesis of a "Block" Polyamino Acid, Poly(Leu/Glu) 50/50 Diblock 15.0 g of NCA-Glu(OMe) (0.08 mol) and 180 ml of dioxane are introduced with stirring into a 1-l reactor. After dissolution, 180 ml of toluene are added and the mixture is brought to 60° C. The IR spectrum of the solution is recorded before adding 0.156 g of benzylamine (1.58 mol %/NCA). The reaction medium rapidly becomes cloudy and, after 40 minutes, the characteristic bands at 1,860 and 1,790 cm$^{-1}$ have disappeared.

After one hour, a solution of 12.5 g of NCA-Leu (0.08 mol) in a dioxane/toluene mixture (15 ml of each) is introduced. Stirring is continued for 18 h (this time has not been optimized). The carbonyl bands have then disappeared. 100 ml of dioxane are added and the reaction medium is homogenized for 1 h. The copolymer is precipitated in 3 l of absolute ethanol with vigorous stirring. It is washed with 1 l of ethanol, filtered, drained and lastly dried at 50° C. under vacuum overnight.

The mass of product recovered is 19.5 g (yield=95%). $^1$H NMR (trifluoroacetic acid-d): 0.85 ppm (CH$_3$-Leu, 6H*0.5); 1.58 (CH$_2$ and CHMe$_2$ Leu, 3H*0.5); 2.10 and 2.22 (CH$_2$-Glu, 2H*0.5); 2.58(CH$_2$-Glu; 2H*0.5); 3.75 (CH$_3$-Glu, 3H*0.5); 4.62 (NCHCO-Leu, 1H*0.5); 4.70 (NCHCO-Glu, 1H*0.5). Reduced viscosity (0.5 g/dl in trifluoroacetic acid) at 25° C.=0.62 dl/g.

The second step of hydrolysis of the methyl esters is identical to that described in Example 1, step 2. Yield 95%. $^1$H NMR (trifluoroacetic acid-d): identical to the starting polymers with one exception, the signal 3.75 (CH$_3$-Glu) is greatly decreased or absent. In the present case, the content of residual esters is less than 1% relative to the glutamate monomers. Reduced viscosity (0.5 g/dl in trifluoroacetic acid) at 25° C.=0.55 dl/g.

Example 3

Synthesis of a "Block" Polyamino Acid, Poly(Glu/Leu/Glu) 29/57/14 Triblock 7.5 g of NCA-Glu(OMe) (0.04 mol) and 180 ml of dioxane are introduced with stirring into a 1-l reactor, After dissolution, 180 ml of toluene are added and the mixture is brought to 60° C. The IR spectrum of the solution is recorded before adding 0.156 g of benzylamine.

After the monomer has disappeared completely, a solution of 12.5 g of NCA-Leu (0.08 mol) in a dioxane/toluene mixture (15 ml of each) is introduced. Stirring is continued for 18 h. 7.5 g of NCA-Glu(OMe) (0.04 mol) are then introduced again and are allowed to react for 12 hours. 100 ml of dioxane are added and the reaction medium is homogenized for 1 h.

The copolymer is precipitated in 3 l of absolute ethanol with vigorous stirring. It is washed with 1 l of ethanol, filtered of, drained and lastly dried at 50° C. under vacuum overnight.

The mass of product recovered is 19.4 g (yield=95%). $^1$H NMR (trifluoroacetic acid-d): 0.85 ppm (CH$_3$-Leu, 6H*0.5); 1.58 (CH$_2$ and CHMe$_2$ Leu, 3H*0.5); 2.10 and 2.22 (CH$_2$-Glu, 2H*0.37); 2.58(CH$_2$-Glu; 2H*0.37); 3.75 (CH$_3$-Glu, 3H*0.37); 4.62 (NCHCO-Leu, 1H*0.5); 4.70 (NCHCO-Glu, 1H*0.37). Reduced viscosity (0.5 g/dl in trifluoroacetic acid) at 25° C.=0.58 dl/g.

The second step of hydrolysis of the methyl esters is identical to that described in Example 1, step 2. $^1$H NMR (trifluoroacetic acid-d): identical to the starting polymer with one exception, the signal at 3.75 (CH$_3$-Glu) is greatly decreased or absent. In the present case, the content of residual esters is less than 1% relative to the glutamate monomers. Reduced viscosity (0.5 g/dl in trifluoroacetic acid) at 25° C.=0.38 dl/g.

II—Formation of Nanoparticles of Polyamino Acids (NDPs) With or Without Incorporation of Active Principles II.1—Influence of the AAN Concentration on Particle Formation Example 4

Formation of Nanoparticles of Poly(Leu/Glu) 30/70, 50/50 and 75/25 having a "Statistical" Structure 100 mg of statistical copolyamino acids of leucine and sodium glutamate, of composition Leu/Glu=30/70 and of molar mass M$_w$=36,000 D, are dispersed in 100 ml of a sodium chloride solution of molarity 10$^{-2}$ mol/l. Irrespective of the pH of the solution of between 4.5 and 12, which may be adjusted by adding hydrochloric acid or sodium hydroxide, the polymer spontaneously forms a colloidal dispersion of nanoparticles. In an acid medium of pH below 4.5, which corresponds to an ionization fraction f equal to 0.05, the lyophilized polymer does not disperse in the solution and remains insoluble.

Table 1 below collates the observations, recorded under the same conditions of dispersion, with the statistical copolyamino acids of leucine and sodium glutamate of compositions Leu/Glu=50/50 and 75/25 and of molar masses M$_w$ equal to 60,000 D and 34,000 D, respectively.

TABLE 1

| POLYAMINO ACIDS | pH RANGE OF EXISTENCE OF THE NANOPARTICLES | IONIZATION FRACTION f OF THE GLUTAMIC ACID |
|---|---|---|
| POLY(LEU/GLU) 30/70 | [4.5–12] | >0.05 |
| POLY(LEU/GLU) 50/50 | [4.7–12] | >0.05 |
| POLY(LEU/GLU) 75/25 | [6.2–12] | >0.30 |

Example 5

Formation of Nanoparticles of Poly(Leu/Glu) 20/80, 40/60 and 50/50 having "Block" Structures 100 mg of block copolyamino acids of leucine and sodium glutamate, of composition Leu/Glu=50/50 and of molar mass $M_w$=14,600 D, are dispersed in 100 ml of a sodium chloride solution of molarity $10^{-2}$ mol/l. Irrespective of the pH of the solution of between 3 and 12, which may be adjusted by adding hydrochloric acid or sodium hydroxide, the polymer spontaneously forms a colloidal dispersion of nanoparticles which scatter light and impart a high turbidity to the solution. The nanoparticles of polymer do not settle out when the solution is left standing for several hours at room temperature of between 15 and 20° C. In an acid medium of pH below 3, the polymer does not disperse in the solution and remains insoluble.

Under the same conditions at a pH of between 3 and 12, poly(Leu/Glu) 20/80 and 40/60 having "block" structures, of molar masses $M_w$ equal to 11,000 D and 15,000 D, respectively, disperse and form colloidal suspensions. The higher the proportion of leucine in the polymer, the more these colloidal suspensions scatter light. At a pH below 3, it is observed, in the same way as for poly(Leu/Glu) 50/50, that the polymers do not disperse and remain insoluble.

Example 6

Solubility of Poly(Leu/Glu) 18/82 having a "Statistical" Structure

This example shows that copolymers of leucine and sodium glutamate of composition Leu/Glu=18/82 do not form nanoparticles since they are completely soluble in water irrespective of the pH≦4.5.

10 mg of lyophilized poly(Leu/Glu) 18/82 are dispersed in 0.5 ml of a sodium chloride solution of molarity $10^{-2}$ mol/l. The polymer has dissolved completely and the solution is clear.

It does not form nanoparticles.

Example 7

Stability of Colloidal Suspensions of Different Poly (Leu/Glu) Polymers 100 mg of statistical copolyamino acids of leucine and sodium glutamate, of compositions Leu/Glu=30/70, 50/50 and 75/25 and of molar mass $M_w$ equal to 36,000 D, 60,000 D and 34,000 D, respectively, are dispersed in 10 ml, 5 ml and 2 ml of a sodium hydroxide solution of molarity $10^{-2}$ mol/l, thereby forming solutions of concentrations 1%, 2% and 5% w/v of each of the polyamino acids. The dispersions are then left in a stability test at room temperature (15–25° C.) for 4 months. At the end of this period, the nanoparticles have not settled out and the diffusion coefficient of the solutions has not changed.

Example 8

Formation of Nanoparticles of Poly(Leu/Glu) 50/50 having a "Statistical" Structure and Having A "Block" Structure, in an Isotonic Phosphate Buffer 100 mg of poly(Leu/Glu) 50/50 polyamino acids, having a "statistical" structure and of molar mass $M_w$ equal to 60,000 D, are dispersed in an isotonic solution of pH 7.4 containing 0.01 mol/l of phosphate buffer, 0.138 mol/l of sodium chloride and 0.0027 mol/l of potassium chloride (PBS, see SIGMA catalogue P4417). The polymer spontaneously forms a colloidal dispersion of nanoparticles which scatter light. The nanoparticles of polymer do not settle out when the solution is left standing for several hours at room temperature of between 15 and 20° C.

Under the same conditions, when 100 mg of poly(Leu/Glu) 50/50 block polyamino acids of molar mass $M_w$ equal to 14,600 D are dispersed in a PBS buffer solution, a suspension of nanoparticles is obtained which is stable at room temperature and which scatters light with a high turbidity.

II.2—Dimensions and Structure of Nanoparticles of Poly (Leu/Glu) Having A "Statistical" Structure and Having A "Block" Structure The nanoparticles of polyamino acids form a colloidal solution. Measurements by static or quasi-elastic light scattering enable the size and the polymer density to be measured in the nanoparticles.

Table 2 below collates measurements performed on statistical polyamino acids of compositions Leu/Glu=30/70 and 50/50 and of molar masses $M_w$ of between 46,000 D and 21,000 D, as well as on the "block" polyamino acid of compositions Leu/Glu 20/80 and 50/50 of molar masses between 11,000 D and 16,300 D. For these measurements, the polyamino acids are dispersed in an isotonic solution of pH 7.4 containing 0.01 mol/l of phosphate buffer, 0.138 mol/l of sodium chloride and 0.0027 mol/l of potassium chloride (see SIGMA catalogue P4417).

TABLE 2

| POLYAMINO ACIDS | MOLAR MASS OF THE POLYAMINO ACID | RADIUS OF GYRATION OF THE PARTICLES IN nm | PERCENTAGE BY WEIGHT (w/v) OF POLYMER IN THE PARTICLES |
| --- | --- | --- | --- |
| Poly(Leu/Glu) 30/70 | 43,000 D | 70 | 1.2 |
| Poly(Leu/Glu) 30/70 | 23,000 D | 58 | 1.0 |
| Poly(Leu/Glu) 50/50 | 46,000 D | 73 | 2.6 |
| Poly(Leu/Glu) 50/50 | 21,000 D | 55 | 4.3 |
| Poly(Leu/Glu) 50/50 block | 14,600 D | 140 | 3.6 |
| Poly(Leu/Glu) 50/50 block | 16,300 D | 120 | 5.5 |
| Poly(Leu/Glu) 20/80 block | 11,000 D | 59 | 5.4 |

The dimensions of the nanoparticles vary with the composition of the polyamino acids. For the same composition, they depend on the diblock or disordered structure of the polyamino acid chains.

Furthermore, the distributions of the diameters of the nanoparticles of polyamino acids are, on the basis of the analyses by quasi-elastic light scattering, monomodal and compressed around their mean value. The widths of the distributions obtained are comparable to or less than that of polystyrene of polydispersity equal to 1.2. The polymer concentration in the nanoparticles is remarkably low and always less than 6% w/v. It depends on the composition and on the diblock or disordered structure of the polyamino acids.

Moreover, observation by electron microscopy (TEM with negative staining) shows that the nanoparticles are spherical or slightly elongated in shape.

II.3—Immunogenicity of the Nanoparticles

Example 9

Immunogenic Power of Nanoparticles of Poly(Leu/Glu) 40/60, 50/50 and 60/40 Block Poly(Leu/Glu) 40/60, 50/50 and 60/40 block, of molar masses equal to approximately 12,000 D, are dispersed in an isotonic solution of pH 7.4 containing 0.01 mol/l of phosphate buffer, 0.138 mol/l of sodium chloride and 0.0027 mol/l of potassium chloride (see SIGMA catalogue P4417).

The polymer concentration is equal to 2.5 mg/ml. The suspensions are turbid and filtered without particular difficulty through a polysulphone membrane of porosity 0.2 µm in order to sterilize them.

The animals used are non-consanguineous OF1 strain mice (group of five mice per polymer tested).

The suspensions of polymers are injected subcutaneously in a volume of 100 µl of suspension (250 µg of polymer) per injection. A first injection is carried out at time D0 and a booster is performed at time D35. Samples are drawn at time D42, that is to say 7 days after the second injection. Blood samples are left for 24 hours at room temperature and are then centrifuged for 10 min at 3,000 rpm.

Sera are analysed by ELISA assay. No anti-polymer antibody was detected in the sera, including at low serum dilutions (1/10).

This example shows that nanoparticles of poly(Leu/Glu) 40/60, 50/50 and 60/40 block do not induce a specific immune response.

II.4—Association of Nanoparticles with Coloured Model Proteins

The encapsulation method is described with haemoglobin and horse heart and *Saccharomyces cerevisea* cytochromes c as model proteins.

The association between the polymer nanoparticles and the proteins is demonstrated by analytical ultracentrifugation. The solutions of polymers and proteins are centrifuged at high speeds, and the advance of the sedimentation fronts of the polymer and the proteins is monitored by measuring the optical density at the wavelengths of 250 nm and 410 nm.

The association between the proteins and the colloidal particles is characterized by the existence of a single sedimentation front corresponding to the superposition of the sedimentation fronts at both wavelengths. In the opposite case, in the absence of association, the sedimentation fronts of the protein and the colloidal particles are separate and do not superpose.

Example 10

Association of Poly(Leu/Glu) 30/70 with Cytochrome c 10 mg of cytochrome c are dissolved in 100 ml of a sodium phosphate buffer solution with a pH equal to 7.2 and of molarity 0.01 mol/l. 100 mg of poly(Leu/Glu) 30/70, of molar mass $M_w$=36,000 D, are then dispersed directly in this solution. Most of the cytochrome c sediments with the colloidal particles of polymer during centrifugation.

Analysis of the optical density of the sedimentation fronts shows that 80% of the cytochrome is associated with the colloidal particles.

Example 11

Association of Poly(Leu/Glu) 50/50 with Cytochrome c 10 mg of cytochrome c are dissolved in 100 ml of a sodium phosphate buffer solution with a pH equal to 7.2 and of molarity 0.01 mol/l. 200 mg of poly(Leu/Glu) 50/50, of molar mass $M_w$=60,000 D, are then dispersed directly in this solution. Most of the cytochrome c sediments with the colloidal particles of polymer during centrifugation.

Analysis of the optical density of the sedimentation fronts shows that 80% of the cytochrome is associated with the colloidal particles.

Example 12

Association of Poly(Leu/Glu) 30/70 with Haemoglobin

In this example, the colloidal suspension of the polyamino acids and the protein is prepared in two different ways, from the same solution as in Example 4, but modifying the order of dissolution.

1—Poly(Leu/Glu) 30/70, of molar mass $M_w$=90,000 D, is dispersed in the haemoglobin solution according to the same conditions as those of Example 4.

Analysis of the colloidal suspension by ultracentrifugation shows the association of the haemoglobin and the polyamino acids in the nanoparticles.

2—Poly(Leu/Glu) 30/70, of molar mass $M_w$=40,000 D, is dispersed in the buffer solution not containing haemoglobin. The colloidal suspension formed is then mixed with the haemoglobin solution. In this case, a large fraction of the haemoglobin, estimated at 80%, is not associated with the nanoparticles of polyamino acids, and analysis by ultracentrifugation shows two sedimentation fronts corresponding to the nanoparticles of polyamino acids and to the haemoglobin, respectively.

The first step of dissolution of the protein before dispersion of the polyamino acid provides, in the case of haemoglobin, for a better encapsulation yield.

II.5—Association of Nanoparticles with Proteins

Example 13

Association of Poly(Leu/Glu) 30/70 in the Presence of Ovalbumin

Poly(Leu/Glu) 30/70, of molar mass $M_w$=90,000 D, is dispersed in a sodium chloride solution under the same conditions as those of Examples 4 or 5 with, in addition, ovalbumin. The characteristics of the colloidal particles analysed by light scattering are identical to those formed in the absence of protein. Hence the protein does not prevent the association of the polyamino acids into nanoparticles, this being the case for protein concentrations which can reach 20% w/v relative to the polyamino acid.

Example 14

Association of Poly(Leu/Glu) 50/50 Block with Insulin

A solution of recombinant human insulin (SIGMA, reference 10259) with a concentration of 1 mg/ml is prepared from an isotonic solution of pH 7.4 containing 0.01 mol/l of phosphate buffer, 0.138 mol/l of sodium chloride and 0.0027 mol/l of potassium chloride. 50 mg of poly(Leu/Glu) 50/50 block, of molar mass equal to 12,400 D, are dispersed in 5 ml of this insulin solution. A very turbid and stable suspension is obtained. By ultrafiltration through a membrane of cut-off 300,000 D (Millipore, Ultrafree-CI. filter), the free insulin in solution is separated from the insulin associated with the nanoparticles and is assayed in the filtrate by HPLC chromatography. The amount of insulin associated with the nanoparticles, equal to 0.65 mg/ml, is thus measured by difference with the amount of free insulin.

Example 15

Association of Poly(Leu/Glu) 50/50 having a "Statistical" Structure with Insulin The procedure is carried out under conditions identical to those of Example 14, using poly(Leu/Glu) 50/50 having a "statistical" structure in place of poly(Leu/Glu) 50/50 block. The amount of insulin associated with the nanoparticles is equal to 0.60 mg/ml.

III—Aggregation of Nanoparticles

III.1—Aggregation by Addition of A Salt

Example 16

Aggregation by Addition of Ammonium Sulphate 100 mg of poly(Leu/Glu) 30/70, of molar mass $M_w$=36,000 D, are dispersed in 200 ml of citric acid/sodium phosphate buffer solution of molarity 0.05 mol/l and pH equal to 5. Concentrated ammonium sulphate solution is added slowly to the dispersion. The volume introduced is sufficiently low compared to that of the dispersion solution, until NDPs have aggregated into MDPs. The MDPs thereby obtained have an average diameter equal to 8 μm.

II.2—Aggregation by Lowering of pH

The side-chain carboxyl functions of the polyamino acids in the nanoparticles are partially ionized. Their neutralization by adding an acid brings about aggregation of the nanoparticles.

The aggregation may be carried out with acids whose dissociation constant (AP) is lower than that of the side-chain carboxyl functions of the polyamino acids.

Example 17

Aggregation by Addition of Hydrochloric Acid

The statistical polyamino acids of compositions Leu/Glu= 30/70, 50/50 and 75/25 and of molar masses $M_w$ equal to 36,000 D, 60,000 D and 34,000 D, respectively, are dispersed in citric acid/sodium phosphate buffer solutions of molarity 0.05 mol/l and pH equal to 5. The concentrations of the polyamino acids are 0.01% w/v for the polyamino acids of compositions Leu/Glu 30/70 and 50/50, and 0.005% w/v for that of composition 75/25.

Aggregation of the nanoparticles in colloidal suspension is carried out by the gradual addition of 0.1 mol/l hydrochloric acid solution until the NDPs have aggregated into MDPs. The results of the measurements of particle size of the MDPs are collated in Table 3 below.

TABLE 3

| POLYAMINO ACIDS | AVERAGE DIAMETER [μm] | DISTRIBUTION |
| --- | --- | --- |
| Poly(Leu/Glu) 30/70 | 20 μm | [2; 100] μm |
| Poly(Leu/Glu) 50/50 | 6 μm | [2; 15] μm |
| Poly(Leu/Glu) 75/25 | 3 μm | [0.5; 8] μm |

III.3—Aggregation by Complexing With A Cationic Polymer

Example 18

Aggregation of Nanoparticles of Poly(Leu/Glu) 50/50 by Complexing with Poly-DL-Lysine The side-chain carboxyl unctions of the polyamino acids in the nanoparticles are partially ionized. Complexing them with a cationic polymer such as polylysine brings about aggregation of the nanoparticles.

10 mg of poly(Leu/Glu) 50/50, of molar mass $M_w$=60,000 D, are dispersed in 100 ml of a sodium phosphate buffer solution of molarity 0.01 mol/l and pH equal to 6. The addition of 15 mg of poly-DL-lysine hydrobromide, of molar mass $M_w$=15,000 D, enables the nanoparticles of polymer to be aggregated into microparticles. The average diameter of the microparticles is between 10 and 20 μm by varying the pH between 2 and 9 by adding hydrochloric acid or sodium hydroxide.

III.4—Encapsulation of Proteins by Aggregation of Nanoparticles

Example 19

Encapsulation of Cytochrome c by Complexing with Poly-DL-Lysine 10 mg of poly(Leu/Glu) 50/50, of molar mass $M_w$=60,000 D, are dispersed in 100 ml of a phosphate buffer solution of molarity 0.01 mol/l with a pH equal to 6 and containing 10 mg of horse heart cytochrome c. The addition of 15 mg of poly-DL-lysine hydrobromide, of molar mass $M_w$=15,000 D, enables the nanoparticles of polymers to be aggregated into microparticles. The microparticles are sedimented by centrifugation; the red colouration of the centrifugation pellet shows that virtually all of the cytochrome has sedimented with the nanoparticles, showing that the cytochrome is encapsulated in the microparticles.

We claim:

1. A non-hollow particles based on polyamino acids for the delivery of active principles wherein in that the particles
    (a) are obtained without the any organic solvent or surfactant, by contacting polyamino acids with an aqueous solution, wherein the polyamino acids
        (1) are linear with α-peptide linkages,
        (2) comprise at least two types of recurring amino acids which are identical or different from one another, selected from the group consisting of a hydrophobic neutral amino acid (AAN), and an amino acid having an ionizable side chain (AAI), at least a portion of the AAI amino acid being in ionized form,
        (3) have a weight average molar mass $M_w$ of not less than 4,000 D, and
        (4) are non-water soluble at acid pH or at a pH between 3 and 12; and
    (b) have an average size between 0.01 μm and 0.5 μm.

2. Particles according to claim 1, wherein the polyamino acids are selected from the group consisting of block and statistical polyamino acids, wherein for the block polyamino acids, the ratio AAN/AAN+AAI mole ratio is≧6% and $M_w$≧5,500 D, and for the statistical polyamino acids the AAN/AAN+AAI mole ratio is≧20% and $M_w$≧10,000 D.

3. Particles according to claim 1, wherein the hydrophobic neutral amino acid is selected from the group consisting of Leu, Ile, Val, Ala, Pro, and Phe or mixtures thereof, and the amino acid having an ionizable side chain is selected from the group consisting of Glu, and Asp, or mixtures thereof.

4. Particles according to claim 1, having an average polyamino acid concentration varying from 0.01 to 25% dry weight.

5. Particles according to claim 4, having an average polyamino acid concentration varying from 0.05 to 10% dry weight.

6. Particles according to claim 1, having an average size between 0.03 and 0.4 μm.

7. Particles according to claim 1, further comprising at least one active principle.

8. Particles according to claim 1, wherein the weight average molar mass $M_w$ of the polyamino acids is not less than 5,000 D.

9. Particles according to claim 2, wherein for the block polyamino acids, the AAN/AAN+AAI mole ratio is≧5% and 6,500 D$\leq M_w \leq$200,000, and for the statistical polyamino acids, the AAN/AAN+AAI mole ratio is$\geq$25% and 20,000 D$\leq M_w \leq$500,000 D.

10. Particles according to claim 9, wherein for the block polyamino acids, 8,000 D$\leq M_w \leq$200,000 and for the statistical polyamino acids is 20,000 D$\leq M_w \leq$150,000 D.

11. Particles according to claim 1, further comprising at least one aggregating agent.

12. Particles according to claim 7, wherein the active principle is medicinal and is selected from the group consisting of
   (a) proteins and peptides selected from the group consisting of haemoglobins, cytochromes, albumins, interferons, antigens, antibodies, calcitonin, erythropoietin, insulin, growth hormones, factor IX and interleukin or mixtures thereof,
   (b) polysaccharides,
   (c) nucleic acids, and
   (d) mixtures thereof.

13. Particles according to claim 7, wherein the active principle is selected from the group consisting of heparin, oligonucleotides of RNA and oligonucleotides of DNA.

14. Particles according to claim 7, wherein the active principle consists of at least one vaccine.

15. Particles according to claim 7, wherein the active principle is composed of at least one plant-protection or cosmetic product.

16. Particles according to claim 1, characterized in that the polyamino acids comprise a single type of comonomer AAN and a single type of comonomer AAI.

17. A method for preparing non-hollow particles, based on polyamino acid(s) which are capable of being used as delivery vehicles for active principles, according to claim 1, comprising the steps of:
   (a) producing a dispersion of polyamino acids in an aqueous liquid free of any organic solvent or surfactant and whose pH has been adjusted to a value chosen in such a way that at least a portion of the amino acid having an ionizable side chain is in ionized form, and
   (b) collecting a colloidal solution of particles from the dispersion.

18. Method according to claim 17, wherein in step (a) at least one active principle is dissolved in the liquid so that a colloidal solution of particles loaded with active principle is obtained.

19. Method according to claim 18, wherein the active principle is dissolved in the liquid before the introduction of the polyamino acids into the liquid.

20. Method according to claim 17, wherein the polyamino acids comprise a single type of comonomer AAN and a single type of comonomer AAI.

21. Method according to claim 17, wherein the liquid in which the dispersion of the polyamino acids is produced is a saline aqueous solution.

22. Method according to claim 17, further comprising a step of aggregating the particles, by adding at least one aggregating agent selected from the group consisting of salts, acids, bases, polymers and ionic polymers.

23. Method according to claim 22, wherein the polymer concentration in the solution is not less than $10^{-2}$% weight/volume.

24. Method according to claim 23, wherein the polymer concentration in the solution is between 0.05 and 30% weight/volume.

25. Method according to claim 23, wherein the polymer concentration in the solution is between 0.5 and 5% weight/volume.

26. Particles according to claim 7, wherein the active principle consists of insulin.

27. A colloidal suspension of non-hollow particles bases on polyaminoacids and intended for the controlled and sustained delivery of active principle(s) wherein said particles:
   (a) are obtained, spontaneously without organic, solvent or surfactant, without pH modification, by contacting polyaminoacids with an aqueous liquid medium, said polyaminoacids being selected among the ones which:
      (1) are linear with α-peptide linkages,
      (2) comprise at least two types of recurring amino acids which:
         are identical or different from one another, and
         are selected from the group consisting of hydrophobic neutral amino acid (AAN) and an amino acid having an ionizable side chain (AAI), at least a portion of the AAI amino acid being in ionized form;
      (3) have a weight average molar mass Mw of no less than 4,000 D, and
      (4) are non-water soluble at acid pH or at a pH between 3 and 12; and
   (b) have an average size between 0.01 m and 0.5 μm.

* * * * *